(12) United States Patent
Kelley

(10) Patent No.: US 7,754,047 B2
(45) Date of Patent: Jul. 13, 2010

(54) CUTTING BALLOON CATHETER AND METHOD FOR BLADE MOUNTING

(75) Inventor: Gregory S. Kelley, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1361 days.

(21) Appl. No.: 10/821,237

(22) Filed: Apr. 8, 2004

(65) Prior Publication Data

US 2005/0228343 A1  Oct. 13, 2005

(51) Int. Cl.
*B29C 65/00* (2006.01)
*B32B 37/00* (2006.01)

(52) U.S. Cl. .................. 156/309.6; 156/308.2; 606/159

(58) Field of Classification Search ........................ None
See application file for complete search history.

(56) References Cited

U.S. PATENT DOCUMENTS

| | | | |
|---|---|---|---|
| 2,127,043 A * | 8/1938 | Most ........................... | 264/274 |
| 2,237,152 A * | 4/1941 | Larmour .................. | 156/303.1 |
| 2,816,552 A | 12/1957 | Hoffman | |
| 3,098,266 A * | 7/1963 | Oehmig ........................ | 52/213 |
| 3,174,851 A | 3/1965 | Buehler et al. | |
| 3,351,463 A | 11/1967 | Rozner et al. | |
| 3,635,223 A | 1/1972 | Klieman | |
| 3,749,085 A | 7/1973 | Willson et al. | |
| 3,753,700 A | 8/1973 | Harrison et al. | |
| 3,990,453 A | 11/1976 | Douvas et al. | |
| 4,140,126 A | 2/1979 | Choudhury | |
| 4,141,364 A | 2/1979 | Schultze | |
| 4,263,236 A | 4/1981 | Briggs et al. | |
| 4,273,128 A | 6/1981 | Lary | |
| 4,292,974 A | 10/1981 | Fogarty et al. | |
| 4,406,656 A | 9/1983 | Hattler et al. | |
| 4,465,072 A | 8/1984 | Taheri | |
| 4,490,421 A | 12/1984 | Levy | |
| 4,572,186 A | 2/1986 | Gould et al. | |
| 4,574,781 A | 3/1986 | Chin | |
| 4,581,513 A * | 4/1986 | Obara et al. ............. | 219/69.12 |
| 4,608,984 A | 9/1986 | Fogarty | |
| 4,627,436 A | 12/1986 | Leckrone | |

(Continued)

FOREIGN PATENT DOCUMENTS

DE  34 00 416 A1  7/1985

(Continued)

OTHER PUBLICATIONS

Machine translation of JP 05293176 Jun. 2008.*

(Continued)

*Primary Examiner*—John L Goff
(74) *Attorney, Agent, or Firm*—Crompton, Seager & Tufte, LLC.

(57) ABSTRACT

A cutting balloon catheter and methods for making and using the same. The cutting balloon catheter may include a catheter shaft having a balloon coupled thereto. One or more cutting members or blades may be coupled to the balloon. Manufacturing the cutting balloon catheter may include partially submerging or embedding a cutting member within a joining member and attaching the joining member to a balloon. The cutting member may include one or more slots along its base that can interlock with the joining member.

13 Claims, 3 Drawing Sheets

U.S. PATENT DOCUMENTS

| | | |
|---|---|---|
| 4,685,458 A | 8/1987 | Leckrone |
| 4,686,982 A | 8/1987 | Nash |
| 4,696,667 A | 9/1987 | Masch |
| 4,705,517 A | 11/1987 | DiPisa, Jr. |
| 4,723,549 A | 2/1988 | Wholey et al. |
| 4,728,319 A | 3/1988 | Masch |
| 4,747,405 A | 5/1988 | Leckrone |
| 4,748,982 A | 6/1988 | Horzewski et al. |
| 4,781,186 A | 11/1988 | Simpson et al. |
| 4,784,636 A | 11/1988 | Rydell |
| 4,787,388 A | 11/1988 | Hofmann |
| 4,790,813 A | 12/1988 | Kensey |
| 4,793,348 A | 12/1988 | Palmaz |
| 4,796,629 A | 1/1989 | Grayzel |
| 4,799,479 A | 1/1989 | Spears |
| RE32,983 E | 7/1989 | Levy |
| 4,867,157 A | 9/1989 | McGurk-Burleson et al. |
| 4,886,061 A | 12/1989 | Fischell et al. |
| 4,887,613 A | 12/1989 | Farr et al. |
| 4,896,669 A | 1/1990 | Bhate et al. |
| 4,909,781 A | 3/1990 | Husted |
| 4,921,483 A | 5/1990 | Wijay et al. |
| 4,921,484 A | 5/1990 | Hillstead |
| 4,936,845 A | 6/1990 | Stevens |
| 4,960,410 A | 10/1990 | Pinchuk |
| 4,966,604 A | 10/1990 | Reiss |
| 4,986,807 A | 1/1991 | Farr |
| 4,987,699 A * | 1/1991 | Gold ............................ 49/375 |
| 4,994,018 A | 2/1991 | Saper |
| RE33,561 E | 3/1991 | Levy |
| 5,009,659 A | 4/1991 | Hamlin et al. |
| 5,015,231 A | 5/1991 | Keith et al. |
| 5,030,201 A | 7/1991 | Palestrant |
| 5,041,125 A | 8/1991 | Montano, Jr. |
| 5,042,985 A | 8/1991 | Elliott et al. |
| 5,047,040 A | 9/1991 | Simpson et al. |
| 5,053,007 A | 10/1991 | Euteneuer |
| 5,053,044 A | 10/1991 | Mueller et al. |
| 5,071,424 A | 12/1991 | Reger |
| 5,074,841 A | 12/1991 | Ademovic et al. |
| 5,074,871 A | 12/1991 | Groshong |
| 5,078,722 A | 1/1992 | Stevens |
| 5,078,725 A | 1/1992 | Enderle et al. |
| 5,084,010 A | 1/1992 | Plaia et al. |
| 5,085,662 A | 2/1992 | Willard |
| 5,087,246 A | 2/1992 | Smith |
| 5,087,265 A | 2/1992 | Summers |
| 5,100,424 A | 3/1992 | Jang et al. |
| 5,100,425 A | 3/1992 | Fischell et al. |
| 5,102,390 A | 4/1992 | Crittenden et al. |
| 5,102,403 A | 4/1992 | Alt |
| 5,116,318 A | 5/1992 | Hillstead |
| 5,135,482 A | 8/1992 | Neracher |
| 5,147,302 A | 9/1992 | Euteneuer et al. |
| 5,152,773 A | 10/1992 | Redha |
| 5,156,594 A | 10/1992 | Keith |
| 5,156,610 A | 10/1992 | Reger |
| 5,158,564 A | 10/1992 | Schnepp-Pesch et al. |
| 5,176,693 A | 1/1993 | Pannek, Jr. |
| 5,178,625 A | 1/1993 | Groshong |
| 5,180,368 A | 1/1993 | Garrison |
| 5,192,291 A | 3/1993 | Pannek, Jr. |
| 5,196,024 A | 3/1993 | Barath |
| 5,196,025 A | 3/1993 | Ranalletta et al. |
| 5,209,749 A | 5/1993 | Buelna |
| 5,209,799 A | 5/1993 | Vigil |
| 5,224,945 A | 7/1993 | Pannek, Jr. |
| 5,226,430 A | 7/1993 | Spears et al. |
| 5,226,887 A | 7/1993 | Farr et al. |
| 5,226,909 A | 7/1993 | Evans et al. |
| 5,242,396 A | 9/1993 | Evard |
| 5,248,311 A | 9/1993 | Black et al. |
| 5,250,059 A | 10/1993 | Andreas et al. |
| 5,295,959 A | 3/1994 | Gurbel et al. |
| 5,300,025 A | 4/1994 | Wantink |
| 5,312,425 A | 5/1994 | Evans et al. |
| 5,318,576 A | 6/1994 | Plassche, Jr. et al. |
| 5,320,634 A | 6/1994 | Vigil et al. |
| 5,328,472 A | 7/1994 | Steinke et al. |
| 5,336,234 A | 8/1994 | Vigil et al. |
| 5,342,301 A | 8/1994 | Saab |
| 5,342,307 A | 8/1994 | Euteneuer et al. |
| 5,346,505 A | 9/1994 | Leopold |
| 5,350,361 A | 9/1994 | Tsukashima et al. |
| 5,372,601 A | 12/1994 | Lary |
| 5,395,361 A | 3/1995 | Fox et al. |
| 5,399,164 A | 3/1995 | Snoke et al. |
| 5,403,334 A | 4/1995 | Evans et al. |
| 5,409,454 A | 4/1995 | Fischell et al. |
| 5,411,466 A | 5/1995 | Hess |
| 5,411,478 A | 5/1995 | Stillabower |
| 5,415,654 A | 5/1995 | Daikuzono |
| 5,417,653 A | 5/1995 | Sahota et al. |
| 5,417,703 A | 5/1995 | Brown et al. |
| 5,423,745 A | 6/1995 | Todd et al. |
| 5,425,711 A | 6/1995 | Ressemann et al. |
| 5,425,712 A | 6/1995 | Goodin |
| 5,437,659 A | 8/1995 | Leckrone |
| 5,441,510 A | 8/1995 | Simpson et al. |
| 5,449,343 A | 9/1995 | Samson et al. |
| 5,456,666 A | 10/1995 | Campbell et al. |
| 5,456,681 A | 10/1995 | Hajjar |
| 5,458,572 A | 10/1995 | Campbell et al. |
| 5,478,319 A | 12/1995 | Campbell et al. |
| 5,487,730 A | 1/1996 | Marcadis et al. |
| 5,496,308 A | 3/1996 | Brown et al. |
| 5,507,760 A | 4/1996 | Wynne et al. |
| 5,507,761 A | 4/1996 | Duer |
| 5,514,092 A * | 5/1996 | Forman et al. ......... 604/101.03 |
| 5,522,818 A | 6/1996 | Keith et al. |
| 5,522,825 A | 6/1996 | Kropf et al. |
| 5,538,510 A | 7/1996 | Fontirroche et al. |
| 5,542,924 A | 8/1996 | Snoke et al. |
| 5,549,556 A | 8/1996 | Ndondo-Lay et al. |
| 5,554,121 A | 9/1996 | Ainsworth et al. |
| 5,556,405 A | 9/1996 | Lary |
| 5,556,408 A | 9/1996 | Farhat |
| 5,569,277 A | 10/1996 | Evans et al. |
| 5,571,087 A | 11/1996 | Ressemann et al. |
| 5,616,149 A | 4/1997 | Barath |
| 5,628,761 A | 5/1997 | Rizik |
| 5,643,209 A | 7/1997 | Fugoso et al. |
| 5,643,296 A | 7/1997 | Hundertmark et al. |
| 5,649,941 A | 7/1997 | Lary |
| 5,662,671 A | 9/1997 | Barbut et al. |
| 5,669,920 A | 9/1997 | Conley et al. |
| 5,681,336 A | 10/1997 | Clement et al. |
| 5,697,944 A | 12/1997 | Lary |
| 5,713,913 A | 2/1998 | Lary et al. |
| 5,718,684 A | 2/1998 | Gupta |
| 5,720,724 A | 2/1998 | Ressemann et al. |
| 5,728,123 A | 3/1998 | Lemelson et al. |
| 5,743,875 A | 4/1998 | Sirhan et al. |
| 5,759,191 A | 6/1998 | Barbere |
| 5,769,819 A | 6/1998 | Schwab et al. |
| 5,769,865 A | 6/1998 | Kermode et al. |
| 5,792,158 A | 8/1998 | Lary |
| 5,797,935 A | 8/1998 | Barath |
| 5,800,450 A | 9/1998 | Lary et al. |
| 5,820,594 A | 10/1998 | Fontirroche et al. |
| 5,824,173 A | 10/1998 | Fontirroche et al. |
| 5,827,201 A | 10/1998 | Samson et al. |
| 5,827,225 A | 10/1998 | Ma Schwab |
| 5,827,310 A | 10/1998 | Mann et al. |

| | | |
|---|---|---|
| 5,895,402 A | 4/1999 | Hundertmark et al. |
| 5,895,406 A * | 4/1999 | Gray et al. ................ 623/1.15 |
| 5,921,958 A | 7/1999 | Ressemann et al. |
| 5,931,819 A | 8/1999 | Fariabi |
| 5,993,469 A | 11/1999 | McKenzie et al. |
| 5,997,557 A | 12/1999 | Barbut et al. |
| 6,010,521 A | 1/2000 | Lee et al. |
| 6,024,722 A | 2/2000 | Rau et al. |
| 6,030,371 A | 2/2000 | Pursley |
| 6,039,699 A | 3/2000 | Viera |
| 6,066,149 A | 5/2000 | Samson et al. |
| 6,068,623 A | 5/2000 | Zadno-Azizi et al. |
| 6,110,192 A | 8/2000 | Ravenscroft et al. |
| 6,117,153 A | 9/2000 | Lary et al. |
| 6,139,510 A | 10/2000 | Palermo |
| 6,142,975 A | 11/2000 | Jalisi et al. |
| 6,165,140 A | 12/2000 | Ferrera |
| 6,165,167 A | 12/2000 | Delaloye |
| 6,165,292 A | 12/2000 | Abrams et al. |
| 6,168,571 B1 | 1/2001 | Solar et al. |
| 6,179,851 B1 | 1/2001 | Barbut et al. |
| 6,190,332 B1 | 2/2001 | Muni et al. |
| 6,193,686 B1 | 2/2001 | Estrada et al. |
| 6,213,957 B1 | 4/2001 | Milliman et al. |
| 6,217,549 B1 | 4/2001 | Selmon et al. |
| 6,217,567 B1 | 4/2001 | Zadno-Azizi et al. |
| 6,221,006 B1 | 4/2001 | Dubrul et al. |
| 6,241,690 B1 | 6/2001 | Burkett et al. |
| 6,254,550 B1 | 7/2001 | McNamara et al. |
| 6,258,108 B1 | 7/2001 | Lary |
| 6,283,743 B1 | 9/2001 | Traxler et al. |
| 6,306,105 B1 | 10/2001 | Rooney et al. |
| 6,306,151 B1 | 10/2001 | Lary |
| 6,309,399 B1 | 10/2001 | Barbut et al. |
| 6,344,029 B1 | 2/2002 | Estrada et al. |
| 6,355,016 B1 | 3/2002 | Bagaoisan et al. |
| 6,383,146 B1 | 5/2002 | Klint |
| 6,387,075 B1 | 5/2002 | Stivland et al. |
| 6,394,995 B1 | 5/2002 | Solar et al. |
| 6,398,798 B2 | 6/2002 | Selmon et al. |
| 6,409,863 B1 | 6/2002 | Williams et al. |
| 6,425,882 B1 | 7/2002 | Vigil |
| 6,471,673 B1 | 10/2002 | Kastenhofer |
| 6,471,713 B1 | 10/2002 | Vargas et al. |
| 6,533,754 B1 | 3/2003 | Hisamatsu et al. |
| 6,544,276 B1 | 4/2003 | Azizi |
| 6,562,062 B2 | 5/2003 | Jenusaitis et al. |
| 6,602,265 B2 | 8/2003 | Dubrul et al. |
| 6,632,231 B2 | 10/2003 | Radisch, Jr. |
| 7,147,619 B2 * | 12/2006 | Lim et al. .............. 604/103.06 |
| 2002/0010489 A1 | 1/2002 | Grayzel et al. |
| 2003/0040770 A1 * | 2/2003 | Radisch, Jr. ................ 606/194 |
| 2003/0163148 A1 | 8/2003 | Wang et al. |

FOREIGN PATENT DOCUMENTS

| | | |
|---|---|---|
| DE | 34 02 573 A1 | 8/1985 |
| DE | 35 19 626 A1 | 12/1986 |
| EP | 0 291 170 A1 | 11/1988 |
| EP | 0 414 350 A1 | 2/1991 |
| EP | 0 565 799 A1 | 10/1993 |
| EP | 0 784 966 A1 | 7/1997 |
| EP | 0 792 656 A1 | 9/1997 |
| GB | 1 547 328 | 6/1979 |
| JP | 05293176 A * | 11/1993 |
| WO | WO 90/07909 A1 | 7/1990 |
| WO | WO 91/17714 A1 | 11/1991 |

OTHER PUBLICATIONS

Lary, Banning G., "A Method to Create and Correct Stenosis of a Coronary Artery," *Archives of Surgery*, Nov. 1966, vol. 93, pp. 828-830.

Lary, Banning G., et al., "A Method for Creating a Coronary-Myocardial Artery," *Surgery*, Jun. 1966, vol. 59, No. 6, pp. 1061-1064.

Lary, Banning G., "An Epicaridal Purse String Suture for Closing Coronary Arteriotomy," *The American Surgeon*, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow," *Archives of Surgery*, Sep. 1963, vol. 87, pp. 424-427.

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., "Method for Increasing the Diameter of Long Segments of the Coronary Artery," *The American Surgeon*, Jan. 1966, vol. 32, No. 1, pp. 33-35.

Lary, Banning G., et al., "Myocardial Revascularization Experiments Using the Epicardium," *Archives of Surgery*, Jan. 1969, vol. 98, pp. 69-72.

Lary, Banning G., "Onlay Vein Graft for the Correction of Coronary Artery Obstruction," *Surgery*, Apr. 1966, vol. 59, No. 4, pp. 547-551.

Lary, Banning G., "Surgery for Coronary Artery Disease," *Nursing Clinics of North America*, Sep. 1967, vol. 2, No. 3, pp. 537-542.

Lary, Banning G., et al., "The 'Coronary Myocardial Artery' for Coronary Artery Disease," *Diseases of the Chest*, Apr. 1996, vol. 49, No. 4, pp. 412-419.

U.S. Appl. No. 10/436,216 to Show-Mean Wu, filed May 12, 2003.
U.S. Appl. No. 10/447,766 to Show-Mean Steve Wu et al., filed May 29, 2003.

* cited by examiner

US 7,754,047 B2

CUTTING BALLOON CATHETER AND METHOD FOR BLADE MOUNTING

FIELD OF THE INVENTION

The present invention pertains to balloon catheters and methods for making balloon catheters. More particularly, the present invention pertains to angioplasty balloon catheters that include one or more cutting blades coupled to the angioplasty balloon and methods for making cutting balloon catheters.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences because the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated, and the restriction of the vessel is opened.

One of the major obstacles in treating coronary artery disease and/or treating blocked blood vessels is re-stenosis. Evidence has shown that cutting the stenosis, for example, with an angioplasty balloon equipped with a cutting blade during treatment can reduce incidence of re-stenosis. Additionally, cutting the stenosis may reduce trauma at the treatment site and/or may reduce the trauma to adjacent healthy tissue. Cutting blades may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting edges have been developed to attempt to enhance angioplasty treatments. There is an ongoing need for improved angioplasty devices, including cutting angioplasty balloons, and improved methods of treating intravascular stenoses and occlusions. In addition, there is an ongoing need for new methods for making cutting balloon catheters.

BRIEF SUMMARY

The present invention relates to angioplasty balloon catheters. In at least some embodiments, an example balloon catheter may include a catheter shaft having a balloon coupled thereto. One or more cutting members or blades may be coupled to the balloon. A number of manufacturing methods are also disclosed. These methods may include providing a joining member, attaching a cutting blade to the joining member, and attaching the joining member to a balloon. These and other features are described in more detail below.

DETAILED DESCRIPTION

Figure 1:
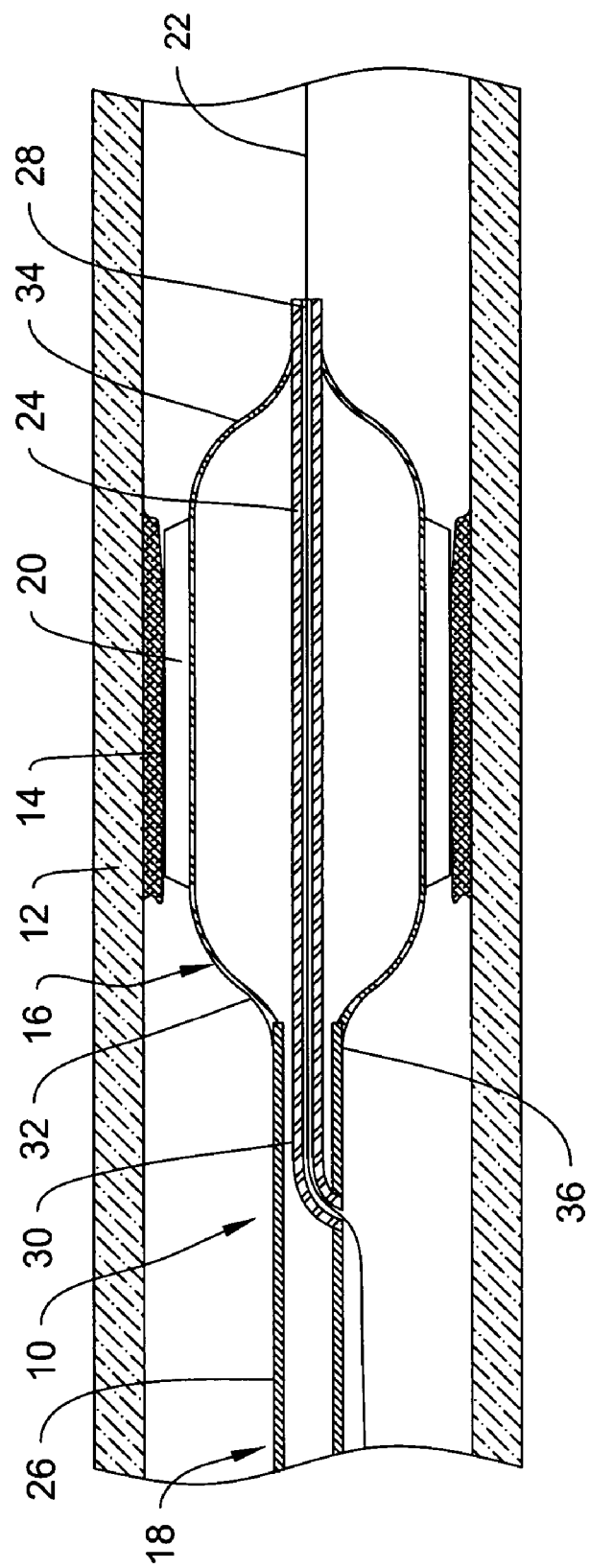
FIG. 1 is a partial cross-sectional side view of an example cutting balloon catheter disposed in a blood vessel.

The following description should be read with reference to the drawings wherein like reference numerals indicate like elements throughout the several views. The detailed description and drawings illustrate example embodiments of the claimed invention.

FIG. 1 is a partial cross-sectional side view of an example catheter 10 disposed in a blood vessel 12 and positioned adjacent an intravascular lesion 14. Catheter 10 may include a balloon 16 coupled to a catheter shaft 18. One or more cutting members or blades 20 may be coupled to balloon 16. In general, catheter 10 may be advanced over a guidewire 22, through the vasculature, to a target area. Balloon 16 can then be inflated to expand lesion 14, and cutting members 20 may cut lesion 14. The target area may be within any suitable peripheral or cardiac vessel lumen location.

One aspect of the invention relates to catheters, for example, like catheter 10. Another aspect of the invention relates to methods for making and using catheters, for example, like catheter 10. Some of the methods for making catheters disclosed herein relate to the way cutting members 20 are attached to balloon 16. Attaching cutting members 20 to balloon 16 may be accomplished in a number of ways. For example, a joining member 38 (not shown in FIG. 1, best seen in FIG. 2) may be disposed between cutting members 20 and balloon 16. The method for attaching cutting member 20 may include attaching cutting member 20 to joining member 38 and attaching joining member 38 to balloon 16. In some embodiments, cutting member 20 may be attached to joining member 38 prior to attaching joining member 38 to balloon 16. In other embodiments, the order may be reversed. A more detailed description of some of the methods for coupling cutting members 20 with balloon 16 is provided below.

Cutting members 20 may made from any suitable material such as a metal, metal alloy, polymer, metal-polymer composite, and the like, or any other suitable material. For example, cutting member 20 may be made from stainless steel such as 304V, 304L, or 316L stainless steel. In some other embodiments, cutting member 20 is made from an iron-cobalt-nickel alloy such as Aermet®100, which is commercially available from Carpenter Technology Corporation. Some examples of other suitable materials are listed below in relation to balloon 16 and shaft 18. Cutting members 20 may vary in number, position, and arrangement about balloon 16. For example, catheter 10 may include one, two, three, four, five, six, or more cutting members 20 that are disposed at any position along balloon 16 and in a regular, irregular, or any other suitable pattern.

Balloon 16 may be made from typical angioplasty balloon materials including polymers such as polyethylene terephthalate (PET), polyetherimid (PEI), polyethylene (PE), etc. Some other examples of suitable polymers, including lubricious polymers, may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP.

Balloon 16 may be configured so that it includes one or more "wings" or wing-shaped regions when balloon 16 is deflated. These wings may appear as a plurality of alternating inward and outward radial deflections in balloon 16 when balloon 16 is deflated. These wings may be desirable for a number of reasons. For example, by including balloon 16 with wings, balloon 16 may have more predictable and consistent re-folding characteristics. Additionally, the wings may be configured so that cutting members 20 can be positioned at the inward-most positions of the deflated balloon 16. This arrangement allows cutting members 20 to be positioned more closely to shaft 18 when balloon 16 is deflated. Accordingly, cutting members 20 can be moved away from the vessel walls where they might otherwise result in contact and, possibly, damage to healthy tissue during movement of catheter 10 within a body lumen. Additionally, alternating the wings and cutting members 20 as well as positioning cutting members 20 relatively close to shaft 18 may allow the wings to fold over and cover cutting members 20 when balloon 16 is deflated. Again, this feature may reduce the exposure of cutting members 20 to the blood vessel.

Shaft 18 may be a catheter shaft, similar to typical catheter shafts. For example, shaft 18 may include an inner tubular member 24 and outer tubular member 26. Tubular members 24/26 may be manufactured from a number of different materials. For example, tubular members 24/26 may be made of metals, metal alloys, polymers, metal-polymer composites or any other suitable materials. Some examples of suitable metals and metal alloys include stainless steel, such as 300 series stainless steel (including 304V, 304L, and 316L); 400 series martensitic stainless steel; tool steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. Some examples of suitable polymers include those described above in relation to balloon 16. Of course, any other polymer or other suitable material including ceramics may be used without departing from the spirit of the invention. The materials used to manufacture inner tubular member 24 may be the same as or be different from the materials used to manufacture outer tubular member 26. Those materials listed herein may also be used for manufacturing other components of catheter 10, including cutting members 20.

Tubular members 24/26 may be arranged in any appropriate way. For example, in some embodiments inner tubular member 24 can be disposed coaxially within outer tubular member 26. According to these embodiments, inner and outer tubular members 24/26 may or may not be secured to one another along the general longitudinal axis of shaft 18. Alternatively, inner tubular member 24 may follow the inner wall or otherwise be disposed adjacent the inner wall of outer tubular member 26. Again, inner and outer tubular members 24/26 may or may not be secured to one another. For example, inner and outer tubular members 24/26 may be bonded, welded (including tack welding or any other welding technique), or otherwise secured at a bond point. In some embodiments, the bond point may be generally disposed near the distal end of shaft 18. However, one or more bond points may be disposed at any position along shaft 18. The bond may desirably impact, for example, the stability and the ability of tubular members 24/26 to maintain their position relative to one another. In still other embodiments, inner and outer tubular member 24/26 may be adjacent to and substantially parallel to one another so that they are non-overlapping. In these embodiments, shaft 18 may include an outer sheath that is disposed over tubular members 24/26.

Inner tubular member 24 may include an inner lumen 28. In at least some embodiments, inner lumen 28 is a guidewire lumen. Accordingly, catheter 10 can be advanced over guidewire 22 to the desired location. The guidewire lumen may extend along essentially the entire length of catheter shaft 18 so that catheter 10 resembles traditional "over-the-wire" catheters. Alternatively, the guidewire lumen may extend along only a portion of shaft 18 so that catheter 10 resembles "single-operator-exchange" or "rapid-exchange" catheters. Regardless of which type of catheter is contemplated, catheter 10 may be configured so that balloon 16 is disposed over at least a region of inner lumen 28. In at least some of these embodiments, inner lumen 28 (i.e., the portion of inner lumen 28 that balloon 16 is disposed over) may be substantially coaxial with balloon 16.

Shaft 18 may also include an inflation lumen 30 that may be used, for example, to transport inflation media to and from balloon 16. The location and position of inflation lumen 30 may vary, depending on the configuration of tubular members 24/26. For example, when outer tubular member 26 is disposed over inner tubular member 24, inflation lumen 30 may be defined within the space between tubular members 24/26. Moreover, depending on the position of inner tubular member 24 within outer tubular member 26, the shape of lumen 30 (i.e., the shape adjacent shaft 18) may vary. For example, if inner tubular member 24 is attached to or disposed adjacent to the inside surface of outer tubular member 26, then inflation lumen 30 may be generally half-moon in shape; whereas, if inner tubular member 24 is generally coaxial with outer tubular member 26, then inflation lumen 30 may be generally ring-shaped or annular in shape. It can be appreciated that if outer tubular member 26 is disposed alongside inner tubular member 24, then lumen 30 may be the lumen of outer tubular member 26 or it may be the space defined between the outer surface of tubular members 24/26 and the outer sheath disposed thereover.

Balloon 16 may be coupled to catheter shaft 18 in any of a number of suitable ways. For example, balloon 16 may be adhesively or thermally bonded to shaft 18. In some embodiments, a proximal waist 32 of balloon 16 may be bonded to shaft 18, for example, at outer tubular member 26, and a distal waist 34 may be bonded to shaft 18, for example, at inner tubular member 24. The exact bonding positions, however, may vary. It can be appreciated that a section of proximal waist 32 may have sections 36 extending therefrom in order for suitable bonding between balloon 16 and outer tubular member 30.

In addition to some of the structures described above, shaft 18 may also include a number of other structural elements, including those typically associated with catheter shafts. For example, shaft 18 may include a radiopaque marker coupled thereto that may aid a user in determining the location of catheter 10 within the vasculature. In addition, catheter 10 may include a folding spring (not shown) coupled to balloon 16, for example, adjacent proximal waist 32, which may further help in balloon folding and refolding. A description of a suitable folding spring can be found in U.S. Pat. No. 6,425,882, which is incorporated herein by reference.

Figure 2:
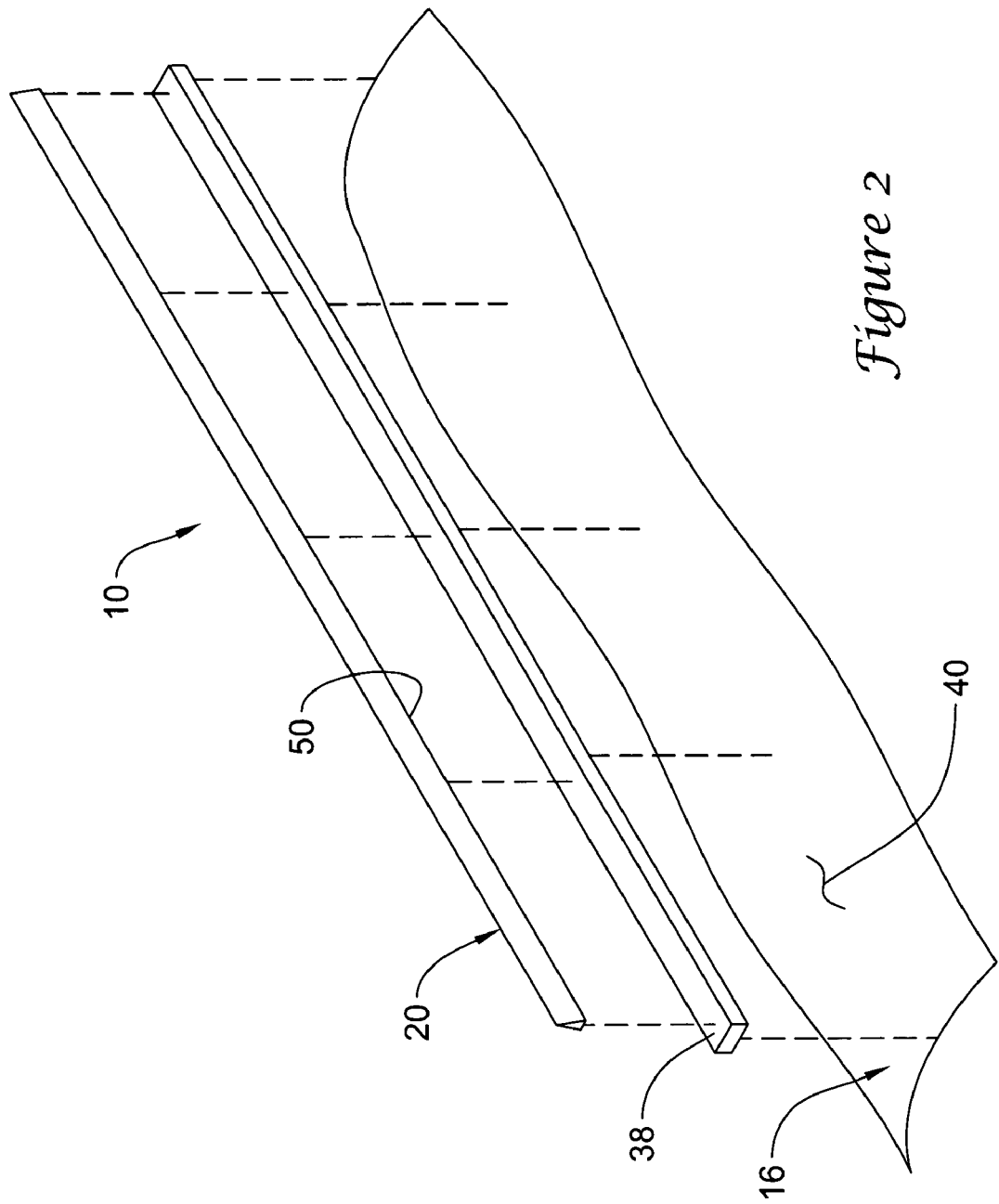
FIG. 2 is a partial perspective view of a cutting member and a joining member for connecting the cutting member to a balloon.

An exploded view depicting joining member 38 and how joining member 38 may be disposed between cutting members 20 and balloon 16 is shown in FIG. 2. In general, joining member 38 may be take the form of a strip, band, ribbon, or the like. Joining member 38 may be made from any suitable material such as any of the polymers described herein. For example, joining member 38 may be made from thermoplastic material (i.e., a material whose viscosity changes with the induction of heat), a thermoplastic-like material, a thermoset material, combinations thereof, or the like. Some examples of these and other suitable polymers are listed above. In some embodiments, joining member 38 may be formed from a generally flexible or soft material that allows the interface or connection between cutting member 20 and balloon 16 to be secure while also being, in some embodiments, somewhat elastic or pliable. For example, joining member 38 may be manufactured from a low durometer polyurethane or any other suitable material (including any of the polymers and other materials disclosed herein). Accordingly, cutting member 20 may be securely coupled to balloon 16 while still being able to move laterally about eight degrees or less. Additionally, different portions of cutting member 20 may be able to bend or flex, while other portions remain essentially unchanged. In other embodiments, joining member 38 may be formed from a somewhat harder material.

In at least some embodiments, joining member 38 can be attached to and disposed between cutting member 20 and balloon 16. For example, joining member 38 can be attached to an outer surface 40 of balloon 16 and to a base 50 of the cutting member 20. The attachment of joining member 38 with cutting member 20 and balloon 16 may be achieved in any appropriate manner, such as by adhesive bonding, casting, thermal bonding, mechanically connecting, welding, brazing, and the like, or in any other suitable way. In some embodiments, attaching joining member 38 with balloon 16 may include bringing joining member 38 into a liquefied, partially liquefied, molten, or partially molten state. According to this embodiment, joining member 38 can be brought into contact with balloon 16 (either while in the liquefied state or just prior to being in the liquefied state), and then become attached to balloon 16 by solidifying. For example, joining member 38 can be heated by directing laser energy onto it prior to bringing joining member 38 into contact with balloon 16. According to this embodiment, the material making up joining member 38 may become molten or partially molten so that it can meld together with balloon 16 upon cooling. Alternatively, joining member 38 and balloon 16 can be brought into contact, and then laser energy can be directed onto joining member 38 so that joining member 38 can liquefy and meld together with balloon 16.

As stated above, a number of alternative methods may be used for attaching joining member 38 to balloon 16. For example, joining member 38 may be solvated or partially solvated (i.e., by adding an appropriate solvent) so that it is brought into a solvated liquid or liquefied state. Some examples of a suitable solvents may include tetra hydro furan, which is appropriate for solvating joining members 38 made from polyurethane or hexa fluoro iso propanol, which is appropriate for solvating joining members 38 made from nylon. While in the solvated liquid state, joining member 38 can be brought into contact with balloon 16 and the "liquid" joining member 38 can be allowed to solidify. Alternatively, the suitable solvent can be added after joining member 38 and balloon 16 are brought into contact. This attaching process may additionally include completely or partially removing the solvent. In addition, it may be useful to partially or completely re-solvate joining member 38 in order to perform additional method steps such as attaching cutting members 20. After performing these later-described method steps, it may be, again, appropriate to remove the solvent. It should be noted that the attachment means need not be the same for the attachment between cutting member 20 and joining member 38 as the means used to attach balloon 16 and joining member 38.

Figure 3:
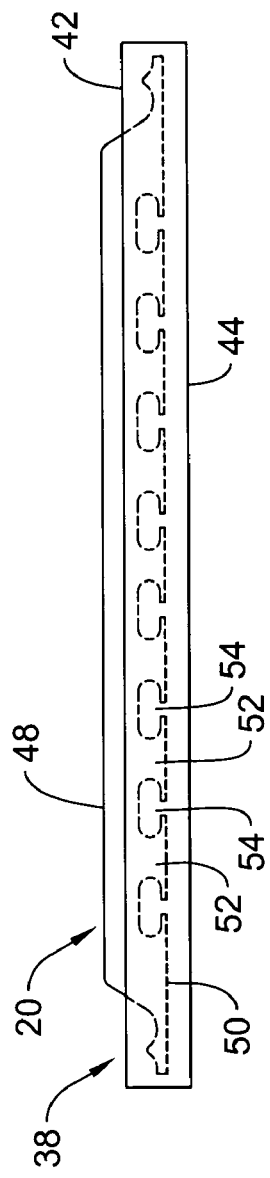
FIG. 3 is a side view of a cutting member and a joining member.

The attachment of cutting member 20 with joining member 38 is shown in FIG. 3. In at least some embodiments, joining member 38 can be brought into a liquid or partially liquefied state in any of the manners described above or in any other suitable manner. For example, joining member 38 may be heated so that it melts or partially melts with the use of a laser that directs laser energy onto a portion of joining member 38 such as a top surface 42. Alternatively, joining member 38 may be brought into a solvated or partially solvated state in a manner similar to what is described above.

With joining member 38 in a partially molten or liquefied state, cutting member 20 can be positioned within joining member 38. In some embodiments, it may be desirable to partially submerge or embed cutting member 20 within joining member 38. This may be accomplished by passing cutting member 20 through a top surface 42 of joining member 38 until cutting member 20 is positioned at the desired depth. The desired depth of insertion can vary, but generally is epitomized by base 50 of cutting member 20 being somewhat spaced from a bottom surface 44 of joining member 38.

Figure 4:
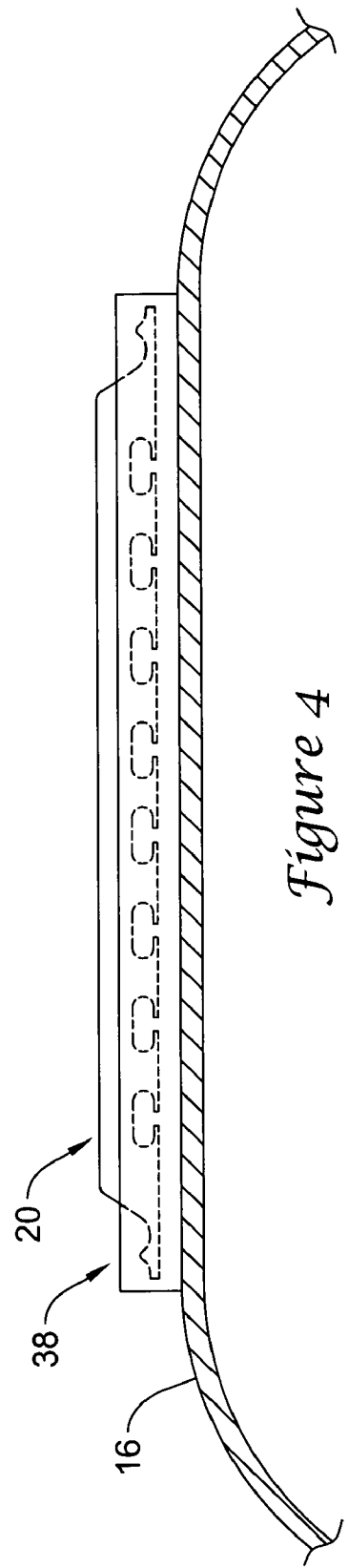
FIG. 4 is a side view of a cutting member, a joining member, and a portion of a balloon.

One advantage of partially submerging cutting member 20 within joining member 38 is that the structure of cutting member 20 allows for a secure, interlocking relationship to be formed. For example, cutting member 20 may include a cutting surface 48 and a series of alternating tabs 52 and holes or openings 54 that are disposed along its base 50. Tabs 52 and openings 54 may be formed in any suitable manner such as with a wire electric discharge milling technique or any other suitable methodology. During the attachment process, the liquefied or partially liquefied joining member 38 can flow into openings 54. Upon solidification, the dispersal of joining member 38 around cutting member 20 can interlock the two structures. This may improve the integrity of the bonding between cutting member 20 with joining member 38. Because joining member 38 will also be bonded with balloon 16 (as shown in FIG. 4), this interlocking relationship can also improve the overall bonding between cutting member 20 with balloon 16. In some embodiments, this interlocking type of bond may be more secure than bonding the various components with adhesives.

It can be appreciated that the step of attaching joining member 38 to cutting member 20 can occur either before or after (or essentially simultaneous with) the step of attaching joining member 38 to balloon 16. For example, joining member 38 may be solvated in order to facilitate attachment of cutting member 20 thereto, and then be partially de-solvated.

The remaining solvated portion of joining member 38 can be utilized to attach the joining member 38 and cutting member 20 subassembly to balloon 16. Once the subassembly is attached, the remaining solvent can be removed.

Collectively, the above discussion elucidates a number of methods for manufacturing catheter 10. For example, one step may include attachment of cutting members 20 with joining member 38 in any of the manners described above. Another step may include attachment of joining member 38 with balloon 16 in any of the manner described above. This step may occur either before or after the step of attaching cutting member 20 with joining member 38. These two attachment steps may further include heating (e.g., with the use of a laser), adding and/or removing a solvent, or any other suitable "liquefying" step as described above.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for manufacturing a cutting balloon catheter, comprising the steps of:
    providing a joining member;
    providing a metallic cutting blade having a longitudinal axis, the cutting blade having a cutting surface and a base having a lower surface, the base including an interlocking structure defined by a plurality of openings formed in the metallic cutting blade along the base such that the openings extend through the lower surface and also an imaginary plane perpendicular to the longitudinal axis which passes through one of the plurality of openings also passes through material of the base located between the opening and the lower surface of the base;
    softening the joining member;
    positioning the cutting blade adjacent the joining member so that the interlocking structure is submerged within and interlocked with the joining member;
    solidifying the joining member so that the cutting blade and the joining member are secured to one another; and
    attaching the joining member and the cutting blade to an angioplasty balloon.

2. The method of claim 1, wherein the step of softening the joining member includes heating the strip.

3. The method of claim 2, wherein heating the joining member includes heating the joining member with a laser.

4. The method of claim 2, wherein heating the joining member includes melting the joining member.

5. The method of claim 1, wherein the step of softening the joining member includes at least partially solvating the joining member with a solvent.

6. The method of claim 1, wherein the step of attaching the joining member and the cutting blade to an angioplasty balloon includes heating the joining member.

7. The method of claim 6, wherein heating includes heating the joining member with a laser.

8. The method of claim 1, wherein the step of attaching the joining member and the cutting blade to an angioplasty balloon includes at least partially solvating the joining member with a solvent.

9. The method of claim 1, further comprising the step of disposing a second cutting blade adjacent the joining member.

10. The method of claim 1, wherein forming a plurality of openings in the metallic cutting blade along the base to define an interlocking surface includes a wire electric discharge milling technique.

11. The method of claim 1, wherein the lower surface of the base is submerged within the joining member to a depth such that the lower surface is spaced from a bottom surface of the joining member.

12. The method of claim 11, wherein the bottom surface of the joining member is bonded to the angioplasty balloon.

13. The method of claim 1, wherein softened material of the joining member flows into the plurality of openings.

* * * * *